United States Patent
Gatzemeyer et al.

(10) Patent No.: US 7,185,383 B2
(45) Date of Patent: *Mar. 6, 2007

(54) BRUSH SECTION FOR A POWERED TOOTHBRUSH

(75) Inventors: John J. Gatzemeyer, Hillsborough, NJ (US); Eyal Eliav, New York, NY (US)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 11/218,839

(22) Filed: Sep. 2, 2005

(65) Prior Publication Data

US 2006/0000038 A1    Jan. 5, 2006

Related U.S. Application Data

(62) Division of application No. 10/260,051, filed on Sep. 27, 2002, now Pat. No. 6,944,901.

(51) Int. Cl.
A46B 13/02   (2006.01)
A61C 17/34   (2006.01)

(52) U.S. Cl. .......................... 15/28; 15/22.1
(58) Field of Classification Search ............. 15/22.1, 15/22.2, 28
See application file for complete search history.

(56) References Cited

U.S. PATENT DOCUMENTS

| | | | |
|---|---|---|---|
| 2,140,307 A | 12/1938 | Belaschk et al. | |
| 5,253,382 A | 10/1993 | Beny | |
| 5,259,083 A | 11/1993 | Stansbury, Jr. | |
| 5,504,958 A | 4/1996 | Herzog | |
| 5,625,916 A | 5/1997 | McDougall | |
| 6,000,083 A | 12/1999 | Blaustein et al. | |
| 6,347,425 B1 | 2/2002 | Fattori et al. | |
| 6,434,773 B1 | 8/2002 | Kuo | |
| 6,510,575 B2* | 1/2003 | Calabrese | 15/22.1 |
| 6,536,066 B2 | 3/2003 | Dickie | |
| 6,574,820 B1 | 6/2003 | DePuydt et al. | |
| 6,725,490 B2* | 4/2004 | Blaustein et al. | 15/22.2 |
| 6,785,929 B2 | 9/2004 | Fritsch et al. | |
| 6,889,401 B2* | 5/2005 | Fattori et al. | 15/22.1 |
| 6,938,294 B2* | 9/2005 | Fattori et al. | 15/22.2 |
| 2003/0066145 A1 | 4/2003 | Prineppi | |
| 2003/0074751 A1* | 4/2003 | Wu | 15/22.1 |
| 2003/0084525 A1* | 5/2003 | Blaustein et al. | 15/22.1 |
| 2003/0084526 A1 | 5/2003 | Brown et al. | |
| 2003/0084528 A1* | 5/2003 | Chan et al. | 15/22.1 |
| 2003/0140437 A1 | 7/2003 | Eliav et al. | |
| 2003/0182744 A1* | 10/2003 | Fattori et al. | 15/22.1 |
| 2003/0196283 A1 | 10/2003 | Eliav et al. | |
| 2004/0010869 A1* | 1/2004 | Fattori et al. | 15/22.1 |
| 2004/0168272 A1* | 9/2004 | Prineppi | 15/28 |

FOREIGN PATENT DOCUMENTS

WO    WO 02/05725    1/2002

* cited by examiner

Primary Examiner—Randall Chin
(74) Attorney, Agent, or Firm—Ellen K. Park

(57) ABSTRACT

A brush section for use in a powered toothbrush, and a powered toothbrush utilizing the brush section are provided. The brush section has a generally disk shaped carrier from which extends at least one finger that has oral care elements, i.e., bristles and elastomeric cleaning members, extending outwardly therefrom to provide increased contact area between the oral care cleaning elements and oral gingival tissue for enhanced massaging thereof.

24 Claims, 7 Drawing Sheets

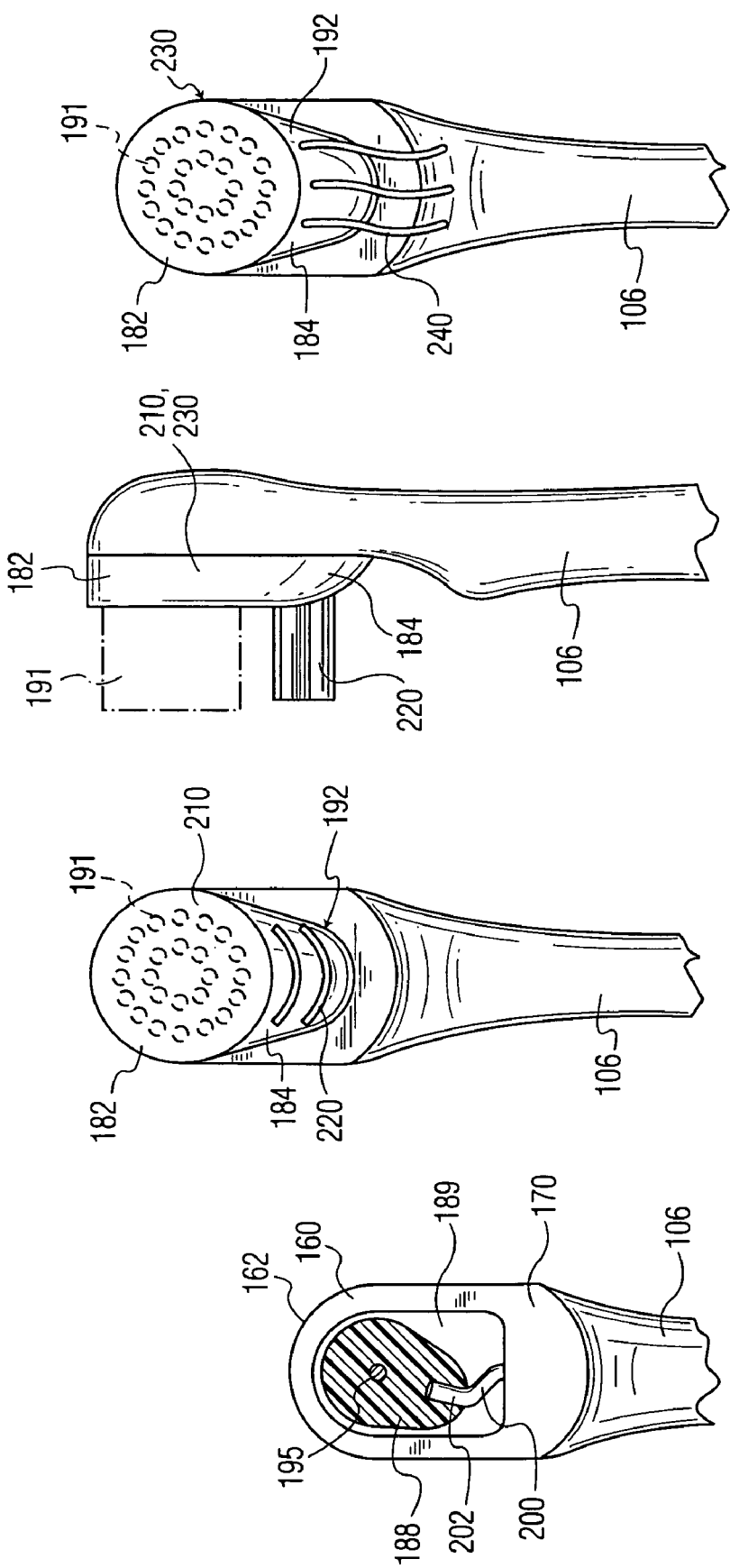

BRUSH SECTION FOR A POWERED TOOTHBRUSH

This is a division of U.S. application Ser. No. 10/260,051, filed Sep. 27, 2002 now U.S. Pat. No. 6,944,901, which is incorporated by reference in its entirety in this present application.

FIELD OF THE INVENTION

The present invention relates to a powered toothbrush, and more particularly, to a brush section having a partially disk-shaped carrier that includes one or more tooth care elements (i.e., bristles or elastomeric members) extending therefrom to provide increased contact with the teeth and/or the oral gingival tissue for enhanced massaging thereof.

DESCRIPTION OF THE RELATED ART

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion will massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of the toothbrush by the user, provide superior cleaning than manual toothbrushes. Typically, powered toothbrushes are powered by disposable or rechargeable batteries that power an electric motor that in turn drives the toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaws. Individual teeth often have extremely complex surfaces, with areas that may be flat, concave, or convex. The more precise conformation between the bristles and the tooth surface, the more effective the toothbrush may be in cleaning, whitening and stimulating.

Known powered toothbrushes typically arrange the bristles in a compact conical or cylindrical pattern on a generally circular, disk-shaped bristle carrier. The powered toothbrush heads are traditionally compact, generally oval in shape and the heads are produced with a flat trimmed bristle pattern. Alternatively, other head shapes and bristle patterns are available.

One example of a powered toothbrush known in the art is depicted in U.S. Pat. No. 5,625,916 to McDougall, which is hereby incorporated by reference in its entirety. The toothbrush shown in McDougall has a disc-shaped bristle carrier. The bristle carrier, and thus the bristles, are driven in a vibrating or oscillating manner. This type of toothbrush is described herein with reference to FIGS. 1A–1C. A toothbrush 5 comprises a handle portion 10 at a proximal end of the toothbrush 5 and a head 11 at a distal end of the toothbrush 5. The handle portion 10 has compartments for containing a powered motor 14 and batteries 15 and 16. The head 11 includes a generally circular bristle holder (carrier) 13. A rotatable shaft 12 extends from the motor 14 to the head 11. A shaft coupling 17 may be located along the shaft 12 and configured to provide for the shaft 12 to be separated at a point between the motor 14 and the head 11. This permits the shaft to be removed from the toothbrush 5, e.g., for cleaning, servicing, or replacement.

The head 11 includes a post 18 that provides a rotational pivot axis for the bristle holder 13 containing bristle tufts 19. The distal end of the shaft 12 has a journal or offset 20 that is radially displaced from the longitudinal axis of the shaft 12. The bristle holder 13 has a slot 22 that receives the offset 20. The offset 20 and slot 22 are configured so as to be oriented toward the intersection of the shaft 12 axis and the longitudinal axis of the post 18. When the motor 14 rotates the shaft 12, the motion of the offset 20 defines a circle about the shaft 12 axis and drivingly engages the slot 22 such that the bristle holder 13 vibrates or oscillates about the post 18 axis through a rotational angle A. The rotational angle A is defined by the displacement of the offset 20 from the shaft 12 axis relative to the diameter of the bristle holder 13.

Powered toothbrushes such as those described immediately above provide advantages over manual toothbrushes, but are subject to various limitations because of the relatively small head size. Providing a rotating or oscillating bristle holder (carrier) with a typical oblong or oval toothbrush head constrains the size of the moving bristle holder, and consequently the area of bristles available for teeth cleaning. Also, when the bristles are placed in contact with the teeth during brushing, there is less bristle contact with adjacent areas, such as the gums, resulting in minimal stimulation of the gingival tissue.

One attempt to overcome the limitations of a small powered bristle area is shown in U.S. Pat. No. 6,000,083 to Blaustein et al. The toothbrush in Blaustein et al. has a bristle area and pattern similar to a manual toothbrush, but an area of the bristles has simply been replaced by a powered bristle section. The result is that the head has a powered or moving bristle section and static bristle section. The limitation of the toothbrush of Blaustein et al. is that the static bristle section provides no better cleaning, whitening or stimulation than a manual toothbrush.

International Application No. PCT/EP01/07615 of Braun GmbH discloses a powered toothbrush with two separate, movable bristle sections. Each bristle section may have a different range and type of motion. The toothbrush of Braun, however, discloses only one powered bristle section. The other unpowered bristle section moves due to a resonance effect imparted by the frequency of the movement of the first bristle section.

This free resonance presents a number of difficulties. First, because any contact between the bristle parts will dampen or cancel any resonance of the unpowered bristle part, the unpowered bristle section "floats" separately from the powered bristle section and the rest of the toothbrush head. This necessitates separation or gaps between them. These gaps expose the internal workings of the head to foreign matter such as water, saliva, toothpaste, and food particles. This foreign matter may interfere with the workings of the unpowered bristle head. For example, the unpowered bristle part is spring-loaded to assist its resonance. Foreign matter may accumulate on or around the spring, interfering with its function. In addition, food particles may remain in the head and may fester and host microorganisms, which are undesirable if not potentially harmful when introduced directly into the mouth.

Another limitation of such a design is that movement of the unpowered bristle section may be damped by contact with the teeth, or lessened when the frequency of the powered section shifts from the resonance frequency. This can occur due to pressure imparted against the powered bristle section by the teeth or gums during brushing. An additional limitation is that the energy imparted to the unpowered bristle section is only a portion of the energy input into the powered section. Therefore, the unpowered bristle section is less effective in cleaning than the powered section, limiting the overall effectiveness of the toothbrush.

Thus, there is a need in the art for a powered toothbrush with increased effectiveness through a larger area of powered or driven bristles than known powered toothbrushes. There is also a need for a toothbrush having increased whitening and stimulation than known toothbrushes. There is a further need for such improved toothbrushes to be comparable in manufacturing and purchasing costs as known powered toothbrushes.

OBJECTS OF THE INVENTION

It is a general object of the present invention to provide a powered toothbrush which avoids the deficiencies and limitation of the known related art.

It is also an object of the present invention to provide a powered toothbrush which enhances the cleaning effectiveness of the toothbrush head.

It is a further object of the present invention to provide a powered toothbrush which enhances the whitening effectiveness of the toothbrush head.

It is yet another object of the present invention to provide a powered toothbrush which enhances the stimulating effectiveness of the toothbrush head.

It is still a further object of the present invention to provide a powered toothbrush which increases the area of powered driven bristles or bristles that are otherwise movable from that of the related art.

Various other objects, advantages and features of the present invention will become readily apparent from the ensuing detailed description and the novel features will be particularly pointed out in the appended claims.

SUMMARY OF THE INVENTION

A powered toothbrush and a brush section for a powered toothbrush are provided. The toothbrush includes a handle portion at a proximal end and a head at the distal end with a neck disposed between the handle portion and the head. The head has a movable bristle carrier that moves across a carrier support platform provided at the head. The bristle carrier has a first portion closest to the distal end of the toothbrush, with the first portion being generally disk-shaped with a circular cross-section. The circular cross-section is partially interrupted by one or more protuberances or fingers extending therefrom in a direction toward the handle and the proximal end of the toothbrush. The bristle carrier has a face extending across the first portion and across the one or more fingers. A plurality of bristle tufts and/or elastomeric members extend outwardly from the face, which has a shape that is neither circular nor oval.

The handle includes a drive mechanism which is drivingly engaged to the bristle carrier, whereby in use the bristle carrier is oscillatingly or reciprocatingly driven, the bristles and/or elastomeric members on the one or more fingers provide increased contact with the oral gingival tissues for enhanced massaging thereof.

Other features and advantages of the present invention will be apparent from the foregoing detailed description when read in conjunction with the accompanying drawings.

BRIEF DESCRIPTION OF THE DRAWINGS

The foregoing and other features of the present invention will be more readily apparent from the following detailed description and drawings of illustrative embodiments of the invention in which:

FIG. 5 is a cross-sectional view taken along the line 5—5 of FIG. 4;

FIG. 6 is a front elevational view of a section of another preferred embodiment of a toothbrush head in accordance with the present invention for use with the powered toothbrush of FIG. 2;

FIG. 7 is a side elevational view of the toothbrush head illustrated in FIG. 6;

FIG. 8 is a front elevational view of a section of another preferred embodiment of a toothbrush head in accordance with the present invention for use with the powered toothbrush of FIG. 2;

DETAILED DESCRIPTION OF CERTAIN PREFERRED EMBODIMENTS OF THE PRESENT INVENTION

Figure 1A:
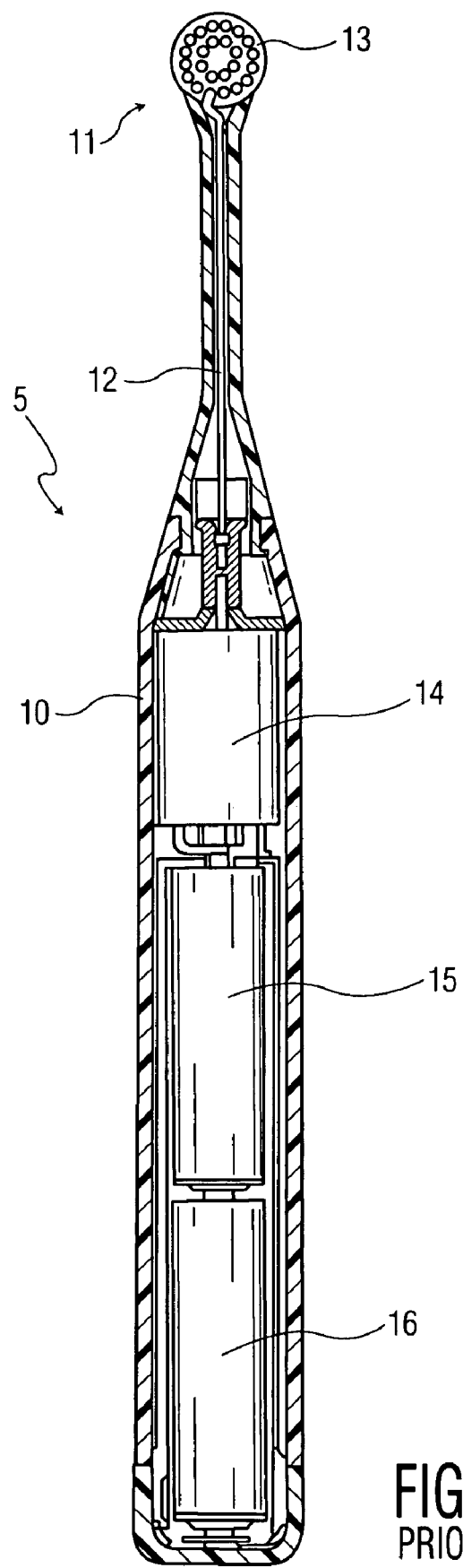
FIG. 1A is a front cross-sectional view of a conventional powered toothbrush including a head.

Referring first to FIGS. 2 through 5, an exemplary powered toothbrush according to a first embodiment is illustrated and generally indicated at 100. The toothbrush 100 includes a handle 102 at a proximal end that defines an interior compartment (not shown) for housing various toothbrush components and a brush section 104 that is defined by a neck 106 that terminates in a head 120 at a distal end of the toothbrush 100. The handle 102 has a free proximal end 108 and an opposite neck end 110. The neck 106 generally extends from a first end 112 to a second end 114 and generally forms the portion of the toothbrush 100 that extends between the handle 102 and the head 120. The neck 106 also defines an interior compartment (not shown) for housing various working components of the toothbrush 100. The head 120 is preferably generally aligned with the longitudinal axis of the toothbrush 100.

In a preferred embodiment, the neck 106 is integrally formed with the handle 102. In an alternate embodiment, the neck 106 is detachable from the handle 102 at the end 110 of the neck 106. In this alternate embodiment, the combined neck 106 and head 120 can be removed from the handle 102 to permit cleaning, servicing and/or interchanging of either the handle 102 or the combined neck 106 and head 120. When the neck 106 is detachable from the handle 102, the first neck end 112 can include a connector (not shown) that is adapted to be detachably joined to the handle 102 using traditional techniques. It will also be appreciated that the point of detachment can be between the head 120 and the neck 106 such that the head 120 is of a refill head type.

It will further be appreciated that the illustrated shapes of the handle 102 and neck 106 are merely exemplary in nature and the handle 102 and/or neck 106 can be formed to have any number of shapes. Preferably, the shape of the handle 102 and the neck 106 are ergonomically pleasing to a user of the toothbrush 100 and provide a toothbrush which is easily gripped, held, and manipulated by the user. The handle 102 may include slightly recessed finger sections 118 which are preferably formed on opposite sides of the handle 102. One recessed finger section 118 is designed to receive the thumb of one hand and the other recessed finger section 118 is designed to receive one or more other fingers of the same hand to thereby assist the user in proper placement of the toothbrush 100. One or more of the recessed finger sections 118 may include ribs or other types of roughened surfaces to further assist gripping by the user. Such surfaces having acceptable frictional characteristics, e.g., rubber, are generally known in the art.

Figure 2:
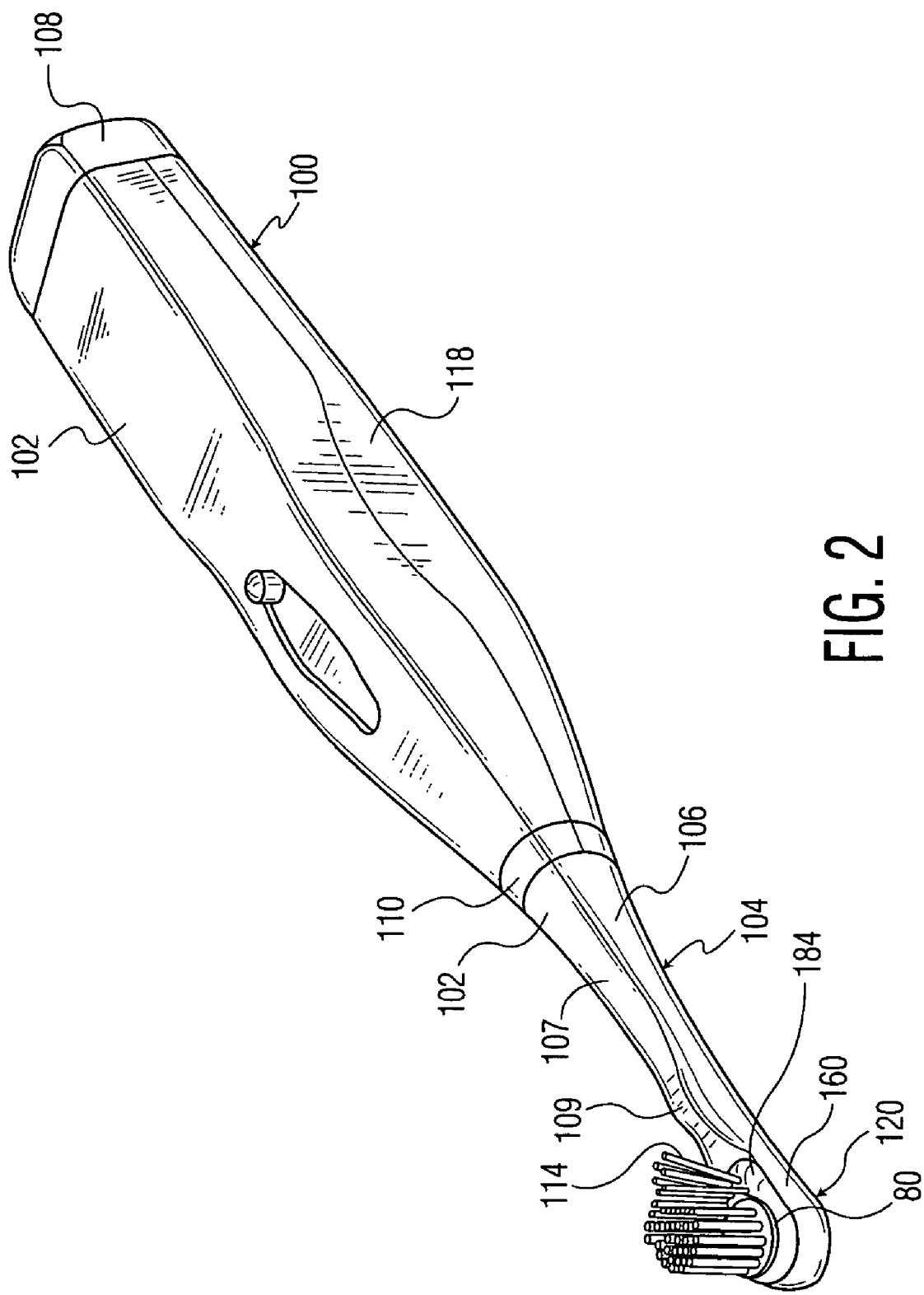
FIG. 2 is a perspective view of a preferred embodiment of a powered toothbrush in accordance with the teachings of the present invention wherein a brush section thereof has a generally egg-shaped face.

According to one embodiment and as best shown in FIG. 2, an upper surface 107 of the neck 106 is contoured to have a slightly raised ridge 109 that slopes downwardly toward the head 120. The head 120 of the toothbrush 100 includes a head base 160 that partially defines an inner compartment 121 (FIG. 4) of the head 120. The head base 160 can be constructed so that it terminates in a rounded distal end 162, which actually defines the distal end of the toothbrush 100. Preferably, the head base 160 is integrally attached to the second end 114 of the neck 106.

The head base 160 also includes a carrier support platform 170 that extends substantially across the head 120 from the neck 106 to the rounded distal end 162. The carrier support platform 170 also partially defines the inner compartment 121 that is formed within the head 120. More specifically, the upper surface 107 of the neck 106 smoothly transitions from the ridge 109 to the sloped portion and then finally to the carrier support platform 170. The carrier support platform 170 includes a first side 172 and an opposite second side 174, each of which is preferably planar in nature. The first side 172 faces the interior compartment 121, which is at least in partial communication with the inner compartment of the neck 106, thereby permitting elements to extend through the inner region of the neck 106 into the inner compartment 121.

The head 120 also includes a movable bristle carrier 180 that has a first portion 182 that is closest to the distal end of the head 106. The first portion 182 is generally disk-shaped with a circular cross-section that is partially interrupted by a protuberance or finger 184 extending therefrom in a direction toward the neck 106. As illustrated, the finger 184 preferably slopes or ramps downward in a direction toward the neck 106 so that a rear portion of the finger 184 seats against the carrier support platform 170. In an alternative embodiment, there are two or more fingers extending from the first portion 182.

The movable bristle carrier 180 thus preferably has a face 186 that extends from and across the first portion 182 to and across the finger 184 from which one or more tooth care elements 190 extend outwardly therefrom. The face 186 preferably has at least one section that is generally sloped. As used herein, the term "tooth care elements" includes any type of structure that is commonly used or is suitable for use in providing oral health benefits (e.g., tooth cleaning, tooth polishing, tooth whitening, massaging, stimulating, etc.) by making intimate contact with portions of the teeth and gums. Such tooth care elements include but are not limited to tufts of bristles that can be formed to have a number of different shapes and sizes and elastomeric cleaning members (see FIGS. 10–14) that can be formed to have a number of different shapes and sizes, or a combination of both tufts of bristles and elastomeric cleaning members. Bristle tufts may be arranged on the face 186 in any configuration and those depicted are exemplary. Moreover, the bristle tufts may be arranged by any conventional method such as stapled, IMT, etc. The bristles tufts may be formed with bristles of the same or different bristle materials (such as nylon bristles, spiral bristles, rubber bristles, etc.). Moreover, while the tooth care elements may be arranged so that they are generally perpendicular to the face 186, some or all of the tooth care elements may be angled at various angles with respect to the face 186. When the face 186 includes bristle tufts, it is thereby possible to select the combination of bristles configurations, bristle materials and bristle orientations to achieve specific intended results and operational characteristics thus maximizing and enhancing cleaning, tooth polishing, tooth whitening, massaging, and stimulation.

While the movable carrier 180 has been defined as a movable bristle carrier 180, it will be understood that the movable carrier 180 is not limited to having only tufts of bristles as a part thereof. The movable carrier 180 may include any number of suitable tooth care elements or any number of combinations of different types of tooth care elements. For example, the movable carrier 180 can include a number of elastomeric members to provide the desired oral health benefits. The elastomeric members may be attached to the movable carrier 180 using conventional techniques, including integrally forming the elastomeric members with the face 186.

Figure 10:
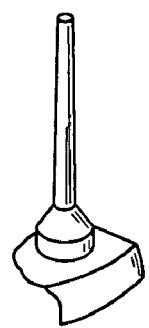
FIG. 10 is a perspective view of an elastomeric contact element having a first configuration and adapted for use in the toothbrush head.
Figure 11:
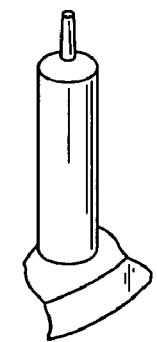
FIG. 11 is a perspective view of an elastomeric contact element having a second configuration and adapted for use in the toothbrush head.
Figure 12:
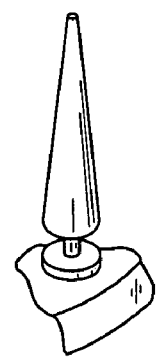
FIG. 12 is a perspective view of an elastomeric contact element having a third configuration and adapted for use in the toothbrush head.
Figure 13:
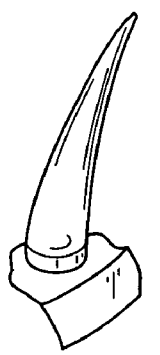
FIG. 13 is a perspective view of an elastomeric contact element having a fourth configuration and adapted for use in the toothbrush head.
Figure 14:
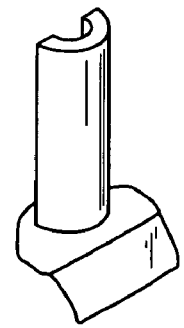
FIG. 14 is a perspective view of an elastomeric contact element having a fifth configuration and adapted for use in the toothbrush head.

FIGS. 10–14 illustrate various exemplary elastomeric members that serve as tooth care elements. FIG. 10 shows an elastomeric tooth care element in the form of a thin spike; FIG. 11 shows an elastomeric tooth care element in the form of a barrel spike; FIG. 12 shows an elastomeric tooth care element in the form of a squeegee point; FIG. 13 shows an elastomeric tooth care element in the form of an angled point; and FIG. 14 shows an elastomeric tooth care element in the form of a section of an elastomeric wall. The elastomeric wall of FIG. 14 may take the form of any number of shapes including but not limited to a linear, planar shape; a zigzag shape; a serpentine shape, etc. In the many contemplated embodiments, the elastomeric tooth care elements may have smooth or rough surface textures. In addition, the wall sections of the elastomeric tooth care elements may be vertically straight, taper inward toward one end or expand toward one end. The tops of the elastomeric tooth care walls may have a planar surface or may have a protrusion (i.e., hump). While the above describes various configurations of elastomeric tooth care elements, those skilled in the art will recognize that virtually any configuration may be achieved.

It will be appreciated that the various features of the described embodiments may apply equally to bristle tufts, elastomeric members, or any combination of bristles and elastomeric members. In a preferred embodiment, the bristle tufts formed in one or more of the first portion 182 or the finger 184 may have uniform heights or non-uniform heights. For example, the bristle tufts disposed in the first portion 182 may have a first height and the bristle tufts disposed in the finger 184 may have a second different height. Further, the heights of the bristle tufts within one of the respective first portion 182 and the finger 184 may have varying heights.

Figure 3:
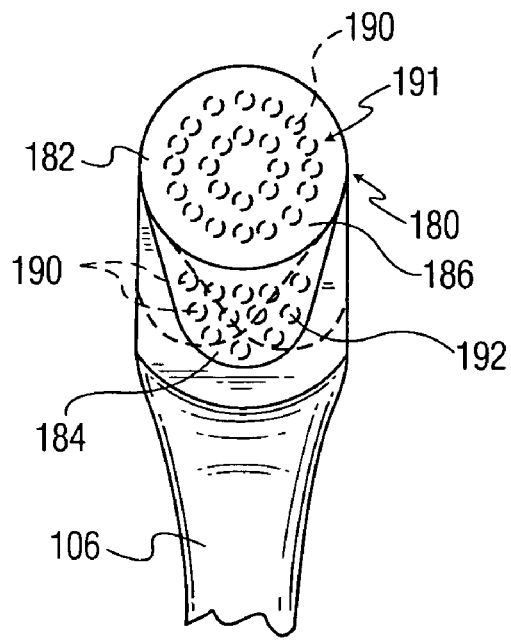
FIG. 3 is a front elevational view of a section of the toothbrush head including the brush section having the generally egg-shaped face illustrated in FIG. 2.
Figure 4:
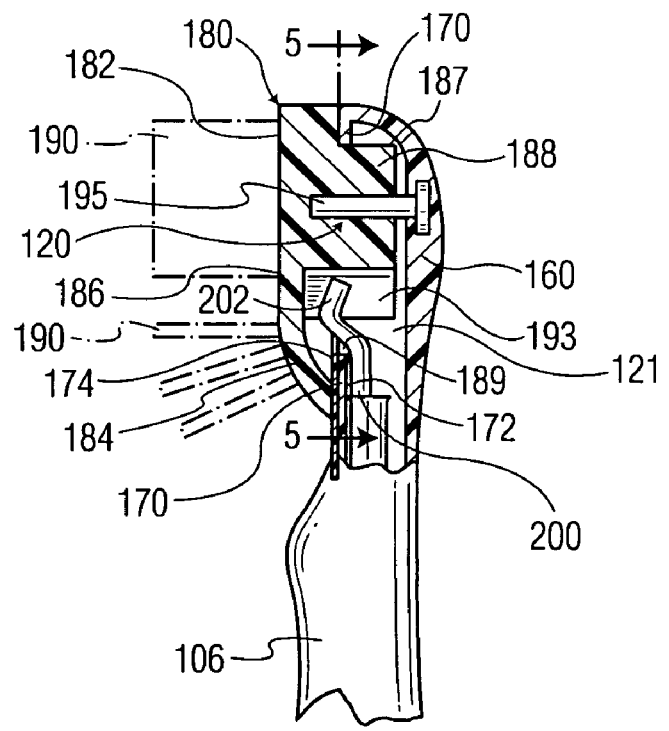
FIG. 4 is a side elevational view of the toothbrush head of FIG. 3 with parts broken away to illustrate the engagement of a drive structure with the brush section.

Referring to FIGS. 2–5, a plurality of bristle tufts 190 may be arranged on the face 186. It will be will understood that the location and arrangement of the bristle tufts 190 in FIGS. 2–4 are merely exemplary and the bristle tufts 190 may be arranged in any number of different arrangements on the face 186. In a preferred embodiment, a first set 191 of bristle tufts is arranged on the first portion 182 (e.g., in a series of concentric rings) and a second set 192 of bristle trufts is arranged on the finger 184 (e.g., in a series of rows). Due to its shape, the movable bristle carrier 180 can be thought of as a generally egg-shaped member arranged such that the end section with the smaller cross-section points toward the neck 106 and the handle 102.

The movable bristle carrier 180 is constructed so as to pivot above the carrier support platform 170, thereby effectuating movement of the bristle tufts 190 that extend outwardly from the face 186. The movement of the movable bristle carrier 180 is preferably an oscillation type movement. As best shown in the cross-sectional view of FIG. 4, one exemplary movable bristle carrier 180 preferably includes a peripheral wall 187 that defines an egg-shaped member and extends downwardly from the face 186. The peripheral wall 187 preferably seats against the carrier support platform 170 but is permitted to move therealong. The movable bristle carrier 180 preferably further has a base section 188 that extends into an opening 189 that is formed in the carrier support platform 170.

The base section 188 includes the axis of which the movable bristle carrier 180 pivots about and is preferably arranged in the head 120 closer to the distal end of the head 120. The base section 188 is most preferably formed in the first portion 182 of the movable bristle carrier 180 as it is preferred for the movable bristle carrier 180 to pivot about the circular first portion 182. Accordingly, the pivot point for the movable bristle carrier 180 is most preferably at the center of the circular first portion 182.

The base section 188 and the opening 189 have complementary shapes to permit movement of the base section 188 within the opening 189. It will be appreciated that the base section 188 may be integrally formed with portions of the peripheral wall 187 or the base section 188 may be formed inside of the peripheral wall 187. In both instances, a portion of the base section 188 preferably extends below the carrier support platform 170 into the inner compartment 121. The base section 188 has one or more slots or openings 193 formed therein. The one or more slots 193 are preferably formed at a peripheral edge of the base section 188 so that each slot 193 can fully receive another member.

A post or the like 195 (see FIG. 5) provides a rotational pivot axis for the movable bristle carrier 180, and more particularly, provides a pivot axis for the base section 188 thereof. The post 195 has a first end disposed in the head base 160 and an upper end of the post 195 is coupled to the base section 188 such that the base section 188 can freely rotate about the axis defined by the post 195.

In a preferred embodiment, the movable bristle carrier 180 may be a significantly hollow member underneath the face 186 with the exception of the base section 188 that extends downwardly from the face 186.

The toothbrush 100 includes a drive mechanism to effectuate movement of certain parts of the toothbrush 100 and more specifically, for causing movement of the movable bristle carrier 180. One exemplary drive mechanism is disclosed in U.S. Pat. No. 5,625,916 to McDougall, which has been previously incorporated herein by reference and includes a rotating drive shaft 200 that extend at least through the neck 106 (i.e., the inner compartment thereof). The drive shaft 200 has one end (not shown) that is operatively connected to a drive member (not shown), such as a motor or any other type of drive device, for imparting movement to the movable bristle carrier 180. The drive shaft 200 has an opposing end 202 forming an offset crank such that the end 202 is not axially aligned with the longitudinal axis of the drive shaft 200. Opposing end 202 is preferably configured to be received in the slot 193 so that the 360° rotational movement of the shaft 200 is transmitted into an oscillating back and forth rotational movement of the movable bristle carrier 180.

It will be appreciated that in one embodiment, the crank end 202 of the drive shaft 200 engages at least a portion of the slot 193 below the plane that contains the carrier support platform 170. The carrier support platform 170 has a slot or opening formed therein to accommodate the rotation of the drive shaft 200 which is fitted through this slot (opening), with the crank end 202 engaging the slot 193 of the movable bristle carrier 180. The carrier support platform 170 is designed to substantially cover the working components (e.g., the drive shaft 200) to prevent ingress of foreign matter, including water, toothpaste, etc., into the inner compartments that house such working components.

Figure 1B:
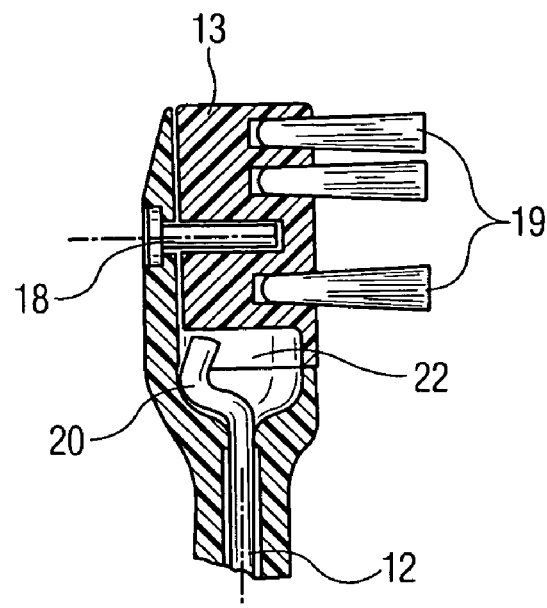
FIG. 1B is a partial cross-sectional side view of the toothbrush head of FIG. 1A.
Figure 1C:
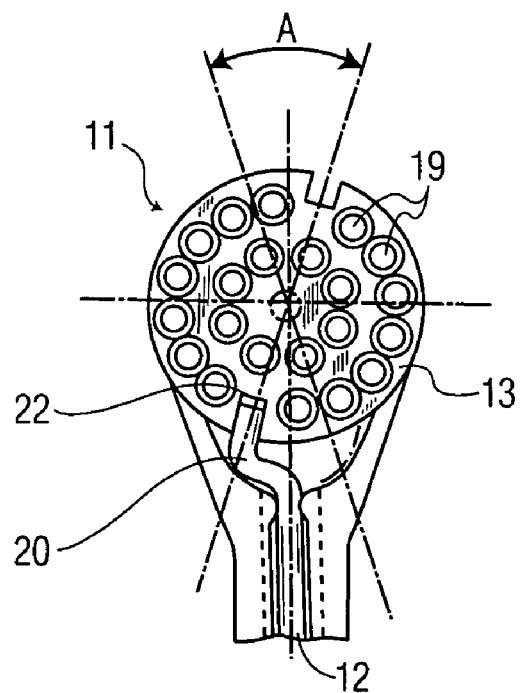
FIG. 1C is a partial cross-sectional front view of the toothbrush head of FIG. 1A.

The drive mechanism for the powered toothbrush 100 may be any type of drive, e.g., a rotating drive, an oscillating drive, an eccentric drive, an unbalanced-generated drive, a drive having one more gearing mechanisms, and/or any other known drive, that is capable of performing the intended function. The drive mechanism may further be realized in the form of an electric motor or other type of motor. The movement generated by the drive mechanism may be imparted to one or more sections of the head 120 or to other elements of the brush section that may be present. The movement may be imparted directly through a driving axle, such as drive shaft 200 or may be imparted through a driving post attached to the driving axle. When the toothbrush 100 includes an oscillating drive mechanism, either identical to or similar to the exemplary drive mechanism illustrated in FIGS. 1A through 1C, the interior compartment of the handle 102 houses a motor operatively connected to the drive shaft 200 and a source to power the motor, such as one or more batteries.

When the drive mechanism is actuated and the drive shaft 200 is rotated, the movement of the crank end 202 imparts an oscillating back and forth movement of the movable bristle carrier 180 through an angle between approximately 10° to 120° and preferably, the movement is through an angle between approximately 10° to 30°. The preferred reduced oscillatory range provides the further benefits of reduced cost and complexity of the toothbrush drive mechanism.

In the embodiment illustrated in FIGS. 2–5, the first set 191 of bristle tufts is preferably arranged on the first portion 182 generally perpendicular to the face 186. Because the finger 184 is sloped downward in the direction toward the neck 106, the second set 192 of bristle tufts is arranged in a series of stepped rows such that at least some of the bristle tufts are angled relative to the bristle tufts in the first set 191.

Referring to FIGS. 6–7, and in an alternate embodiment, the movable bristle carrier 210 has the same construction as the movable bristle carrier 180 except that the movable bristle carrier 210 may include not only bristle tufts but also one or more elastomeric cleaning members. Preferably, in this embodiment, the second set 192 of tooth care elements includes one or more elastomeric members in the shape of upstanding elastomeric walls. Most preferably, a series of elastomeric walls 220 may be securely attached to the finger 184 of the movable bristle carrier 210.

In yet another embodiment, each of the elastomeric walls 220 has an arcuate shape with one elastomeric wall 220 preferably being spaced from the next adjacent elastomeric wall. It will be appreciated that the elastomeric walls 220 may be formed of the same elastomeric material or different elastomeric materials and the heights of the elastomeric walls 220 may be the same or different. In such an alternate embodiment, the heights of the elastomeric walls 220 are preferably such that the tops of the elastomeric walls 220 are contained within the same plane.

Figure 9:
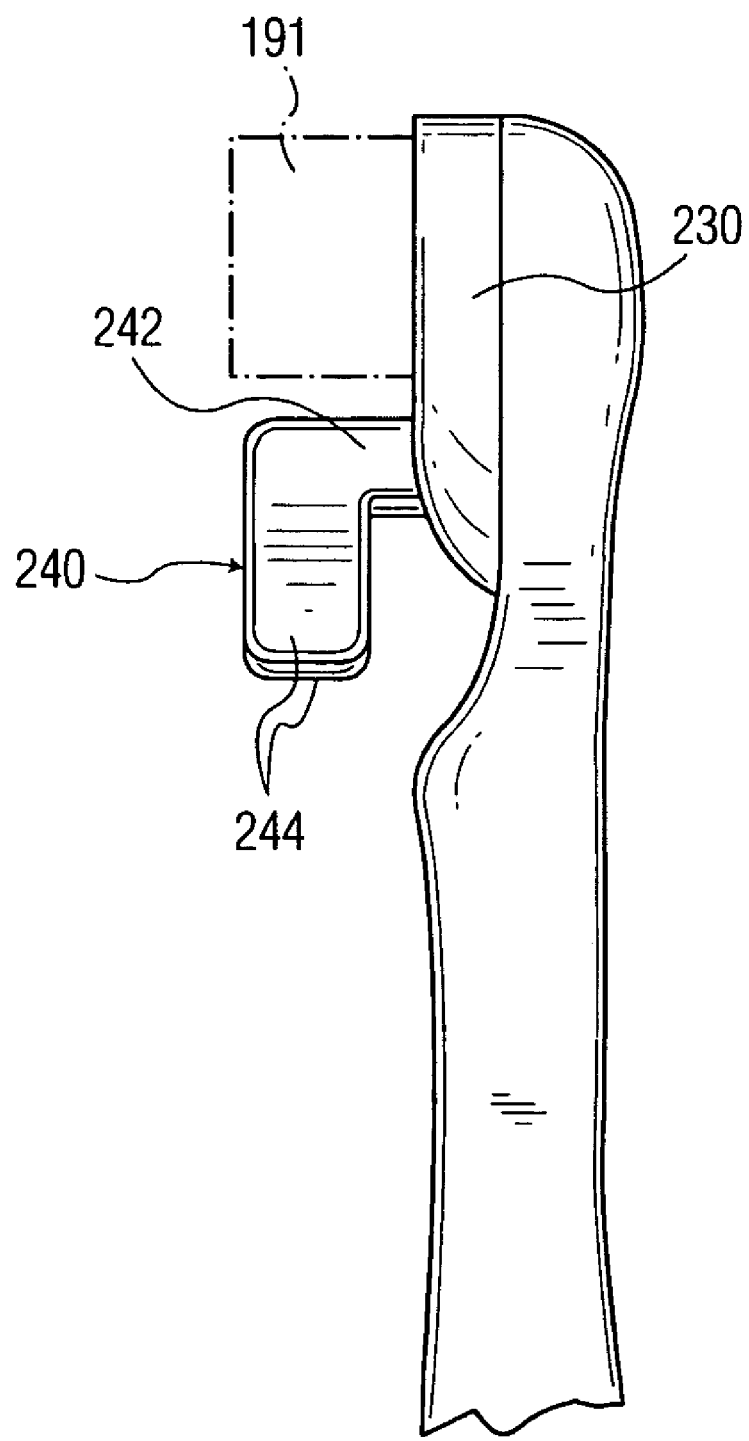
FIG. 9 is a side elevational view of the toothbrush head illustrated in FIG. 8.

FIGS. 8–9 illustrate a movable bristle carrier 230 according to yet another embodiment. The movable bristle carrier 230 is preferably identical to the movable bristle carrier 180 except that the movable carrier 230 preferably includes not only bristles but also one or more elastomeric tooth care elements wherein the second set 192 of tooth care elements includes one or more elastomeric members 240 formed in the shape of extended flags having a generally sinusoidal thickness. Most preferably, a plurality of elastomeric flags 240 may be securely attached at base portions 242 to the finger 184 of the movable bristle carrier 180. The base portion 242 preferably functions as a post for anchoring the elastomeric flag 240 to the finger 184 and a flag body 244 preferably extends outwardly away from the post 242 at an upper section thereof.

While the flag body 244 is illustrated as having a generally rectangular shape, it will be appreciated that the flag body 244 may have any number of different shapes (i.e., triangular, etc.). It will further be appreciated that the elastomeric flags 240 may be formed of the same elastomeric material or of different elastomeric materials and the heights of the elastomeric flags 240 may be the same or different. In the illustrated embodiment, the posts 242 of the elastomeric flags 240 are generally axially aligned; however, the posts 242 may be offset from one another and do not have to be axially aligned with one another.

The toothbrush 100 according to the various embodiments disclosed herein may be made from any number of materials that are suitable for use in oral care products. For example, many of the components that are included in the toothbrush 100 are preferably formed from plastic materials. Accordingly, the handle 102 and head 120 of the powered toothbrush 100 may be molded from polyolefixens-such as polypropylenes and polyethylenes, polyamids such as nylons, and polyesters such as polyethylene terephthalate. Other suitable materials include polymethylmethacrylate, styrene acroylonitrate and cellulose esters, for example cellulose propionate.

When the tooth care elements are in the form of tufts of bristles, the bristles of may be made from a flexible material suitable for dental hygiene. Generally, materials suitable for bristles are polyamides, such as nylon, or polyesters, such as polybutylene terephthalate. When the tooth care elements are in the form of elastomeric members, they may be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide (2 or polyanude 6), polyesters (for example polyester ester or polyether ester), polyurethanes (for example polyesterurethane, polyethenuethane or polyesteretherurethane). In addition, natural or synthetic rubbers can be used.

A powered toothbrush made in accordance with any of the present embodiment offers a number of advantages over conventional powered toothbrushes that are presently available. The movable bristle carrier oscillates back and forth, or moves otherwise, and as the operator brushes his or her teeth, the oscillating tooth care elements (i.e., bristle tufts and/or elastomeric members) contact the surfaces of the teeth and the surrounding areas to deliver enhanced cleaning, tooth polishing, and/or tooth whitening. The egg-shaped face of the movable bristle carrier permits the tooth care elements to be disposed in a number of different patterns and the increased number of tooth care elements provide increased contact with gingival tissues and enhanced massaging thereof. Advantageously, the circular first portion of the movable bristle carrier is orientated at the distal end of the head and the finger extends toward and faces the handle, thereby permitting the movable bristle carrier to pivot without extending distally beyond the underlying head base and permitting a circular arrangement of bristles to be provided at the distal end.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A brush section for a powered toothbrush having a drive device, the brush section comprising:
   a carrier having a first tooth care element region including a face and at least one tooth care element extending from said face;

the carrier further comprising a second tooth care element region extending longitudinally from said first tooth care element region, said second tooth care element region being arcuate shaped substantially downward in the direction of a neck portion and includes at least one elastomeric tooth care element extending therefrom;

wherein said first and second tooth care element regions move in the same path of motion; and wherein said carrier is driven to oscillate about a pivot axis that extends perpendicular to said face of said first tooth care element region.

2. The brush section of claim 1, wherein the carrier is generally egg-shaped.

3. The brush section of claim 1, wherein the first tooth care element region has a planar surface and the second tooth care element region has a sloped surface.

4. The brush section of claim 1, further comprising a head, wherein the head includes a carrier support platform disposed below the carrier.

5. The brush section of claim 1, wherein the second tooth care elements-region comprises a plurality of elastomeric fingers that are angled relative to the at least one tooth care element of the first tooth care element region.

6. The brush section of claim 1, wherein the tooth care elements comprise at least one upstanding elastomeric wall.

7. The brush section of claim 6, wherein the at least one upstanding elastomeric wall comprises a plurality of spaced elastomeric walls.

8. The brush section of claim 7, wherein the plurality of elastomeric walls have different heights.

9. The brush section of claim 1, wherein the first tooth care element region comprises a plurality of bristle tufts.

10. The brush section of claim 1, wherein at least one of the first and second tooth care element regions includes a plurality of elastomeric fingers.

11. The brush section of claim 1, wherein the face extends across both of the first and second tooth care element regions.

12. The brush section of claim 11, wherein said face has a non-circular or non-oval shape.

13. The brush section of claim 1, wherein said second tooth care element region is in the form of a finger member extending longitudinally from the first tooth care element region to the proximal end.

14. A powered toothbrush comprising:
a handle having a distal end and a brush section provided at a proximal end, the brush section further comprising a carrier having a first tooth care element region including a face and at least one tooth care element extending from said face;
the carrier further comprising a second tooth care element region extending longitudinally from said first tooth care element region, said second tooth care element region being arcuate shaped substantially downward in the direction of a neck portion and including at least one elastomeric tooth care element extending therefrom;

wherein said first and second tooth care element regions move in the same path of motion; and wherein said carrier is driven by a drive device to oscillate about a pivot axis that extends perpendicular to said face of said first tooth care element region.

15. The powered toothbrush of claim 14, further comprising a head, wherein the head includes a carrier support platform disposed below the carrier, the carrier support platform having an opening formed therein for receiving a base section of the carrier which engages the drive device for driving the carrier.

16. The powered toothbrush of claim 15, wherein the base section is attached at one end to the face of the carrier and an opposite end extends below the carrier support platform through the opening formed therein.

17. The powered toothbrush of claim 14, wherein the drive device further comprises a drive shaft, and wherein an underside of the second tooth care element region of the carrier has a hollow section to accommodate movement of the drive shaft.

18. The powered toothbrush of claim 14, further comprising a head, wherein the head includes a carrier support platform disposed below the carrier.

19. The powered toothbrush of claim 18, wherein the base section is attached at one end to the face of the carrier and an opposite end extends below the carrier support platform through the opening formed therein.

20. The powered toothbrush of claim 14, wherein the second tooth care elements region comprises a plurality of elastomeric fingers that are angled relative to the at least one tooth care element of the first tooth care element region.

21. The powered toothbrush of claim 14, wherein the tooth care elements comprise at least one upstanding elastomeric wall.

22. The powered toothbrush of claim 21, wherein the at least one upstanding elastomeric wall comprises a plurality of spaced elastomeric walls.

23. The powered toothbrush of claim 22, wherein the plurality of elastomeric walls have different heights.

24. The powered toothbrush of claim 14, wherein at least one of the first and second tooth care element regions includes a plurality of elastomeric fingers.

* * * * *